United States Patent [19]

Laruelle et al.

[11] Patent Number: 5,134,157
[45] Date of Patent: Jul. 28, 1992

[54] AMINO ACID OF CYCLOALIPHATIC ALCOHOLS, PROCESS FOR THEIR PREPARATION AND USE AS DRUGS

[75] Inventors: Claude Laruelle, Villeneuve Loubet; Marcel Lepant, Vence; Bernard Raynier, Cagnes, all of France

[73] Assignee: Panmedica S.A., Carros, France

[21] Appl. No.: 622,124

[22] Filed: Dec. 3, 1990

Related U.S. Application Data

[63] Continuation of Ser. No. 94,600, Sep. 9, 1987, abandoned.

[30] Foreign Application Priority Data

Sep. 16, 1986 [FR] France .................. 86 12915

[51] Int. Cl.$^5$ ............... A61K 31/40; C07D 207/12
[52] U.S. Cl. ..................................... 514/423; 548/534
[58] Field of Search .................. 548/534; 514/423

[56] References Cited

U.S. PATENT DOCUMENTS

| | | | |
|---|---|---|---|
| 4,296,110 | 10/1981 | Johnson | 548/534 X |
| 4,452,989 | 6/1984 | Deckner et al. | 548/534 X |
| 4,639,443 | 1/1987 | Kosley et al. | 514/365 X |
| 4,661,512 | 4/1987 | Laruelle et al. | 514/423 |
| 4,772,601 | 9/1988 | Martin | 548/534 X |
| 4,774,255 | 9/1988 | Black et al. | 548/534 X |

FOREIGN PATENT DOCUMENTS

| | | |
|---|---|---|
| 154472 | 9/1986 | European Pat. Off. |
| 261228 | 7/1911 | Fed. Rep. of Germany . |
| 1510466 | 1/1968 | France . |
| 75913 | 4/1954 | Netherlands . |
| 729550 | 5/1955 | United Kingdom . |
| 1156389 | 6/1969 | United Kingdom . |
| 1436329 | 5/1976 | United Kingdom . |
| 1464985 | 2/1977 | United Kingdom . |

OTHER PUBLICATIONS

Julia et al.; Tetrahedron, 40, (1984), pp. 327–337.
Inamura et al.; C.A., 84 (1976), p. 74612g.
Abe et al.; C.A., 94 (1981), p. 72016y.
Komeyoshi et al.; C.A., 105, (1986), p. 42457w.
Gold et al.; C.A., 84, (1976), p. 40166z.
Humbert; C.A., 87, (1977), p. 189314r.
Unilever N.V., C.A., 88, (1978), p. 158290w.
Lee, THPS–Nov. 1987, vol. 8.

Primary Examiner—Joseph Paul Brust
Attorney, Agent, or Firm—Browdy and Neimark

[57] ABSTRACT

Amino acid esters of cycloaliphatic alcohols of the formula:

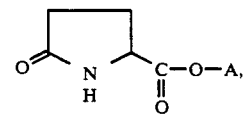

wherein A is cyclohexyl, cyclohexenyl, cyclopentyl and cyclopentenyl, substituted with from one to three radicals which are methyl, ethyl, and/or ethenyl. These amino acid esters have hypolipemic properties.

7 Claims, No Drawings

AMINO ACID OF CYCLOALIPHATIC ALCOHOLS, PROCESS FOR THEIR PREPARATION AND USE AS DRUGS

This application is a continuation of application Ser. No. 07/094,600, filed Sep. 9, 1987, and now abandoned.

The present invention relates to natural amino acid esters of cycloaliphatic alcohols whose ring comprises 5 or 6 hydrocarbon members optionally substituted by hydrocarbon radicals containing one or two carbon atoms, the said compounds having a hypolipemic activity, to the process for their preparation and to the compositions, containing such compounds, which are capable of correcting lipemia disorders. These products correspond to the following general formula (I):

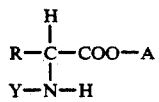

in which:
R represents the residue of a natural α-amino acid or of a simple derivative of the latter, such as the methyl ester, the ethyl ester or a primary amide,
Y is hydrogen or an acetyl, propionyl or benzoyl radical, or alternatively represents, with R, a pyrrolidin-2-one ring determining a pyroglutamic acid ester in the general formula, and
A represents a cycloaliphatic unit selected from the group comprising cyclohexyl, cyclohexenyl, cyclopentyl and cyclopentenyl, optionally substituted by one or more alkyl radicals selected from the following groups: methyl, ethyl, methylene, ethylene and ethenyl.

The study of the synthesis of amino acid esters and their physicochemical properties has long been restricted to the first members of the alcohol series, mainly methyl and ethyl, or to the benzyl esters and the esters of various substituted phenols. The first esters of lower alkanols were also subjected to pharmacological studies, while the benzyl or phenyl esters were synthesized as synthesis intermediates for their particular chemical reactivity, for example the benzyl esters for their ability to undergo hydrogenolysis or the pentachlorophenyl esters for their chemical reactivities.

The interest of amino acid esters of cycloaliphatic alcohols was emphasized by the work of HIROYUKI YAMAMOTO (Biopolymers 9, 41/52—1970), who prepared γ-menthyl glutamate monomers and utilized the properties of the glutamic acid γ-ester to polymerize it.

In his U.S. Pat. No. 3,899,585, AJINOMOTO claimed the $C_{12}$ to $C_{16}$ linear alkyl esters of pyroglutamic acid and their bactericidal activity. The physical properties of these same pyroglutamic acid esters were utilized by K. THOMAE in his German Patent 2 102 172 to prepare adjuvants for creams and lotions.

Finally, in its French Addition no. 2357544, UNILEVER claimed the soothing topical properties of menthyl pyroglutamate, especially in the treatment of sunburn.

The Applicant Company has found, surprisingly, that amino acid esters of cycloaliphatic alcohols with a particular structure, including the terpene alcohols, some of which have been described for their topical use, have very advantageous pharmacological activities when used by a general mode of administration.

These activities are particularly apparent in the correction of lipemia disorders by lowering the blood cholesterol level in the case of hypercholesterolemia, the mechanism being due to the inhibitory action towards hydroxymethylglutaric coenzyme A reductase and, in some cases, to partial inhibition of acetyl coenzyme acyl transferase.

In the cycloaliphatic alcohols series, the term "terpene alcohol" includes alcohols containing the cyclohexyl ring which may or may not be substituted and may or may not be bridged, inter alia menthol, terpinenol, isopulegol, terpineol, linnolenol, carveol and also borneol, fenchyl alcohol and myrtenol.

The term "natural amino acids" includes the alpha-amino acids which make up proteins, i.e. they have a chiral site in the α-position determining L and D isomers, the L isomer being the more universally widespread in nature. In certain cases, the racemic form of the amino acid will be included.

The term "amino acids" also includes the simplest derivatives such as the lower alkyl monoesters of dicarboxylic amino acids or the N-acetyl, N-propionyl and N-benzoyl derivatives on the nitrogen carried by the carbon in the α-position.

The following may be mentioned among the most common amino acids: glycine, alanine, valine, leucine, proline, threonine, serine, phenylalanine, cysteine, cystine, tyrosine, aspartic acid, asparagine, glutamic acid, glutamine, pyroglutamic acid, tryptophan, 5-hydroxytryptophan, arginine, lysine, ornithine, hydroxyprolines, delta-hydroxylysine, α-aminoadipic acid, N-ω-methylarginines, β-hydroxyphenylalanine, β-hydroxytyrosine and β-hydroxyglutamic acid.

The term "cycloaliphatic" is understood as meaning the cyclopentyl, methylcyclopentyl, dimethylcyclopentyl, ethenylmethylcyclopentyl, trimethylcyclopentenyl, cyclopentenyl, methylcyclopentenyl, cyclohexyl, methylcyclohexyl, dimethylcyclohexyl, trimethylcyclohexyl, ethylcyclohexyl, ethenylcyclohexyl, dimethylcyclohexenyl and trimethylcyclohexenyl units.

In the case of substituted cycloaliphatics having both the cis and trans isomeric forms, the pure cis form and the pure trans form will be included, as well as their mixtures in various proportions.

In the initial step, a derivative, protected on the nitrogen in the α-position, of the desired amino acid is reacted with the alcohol in solution in an inert solvent. The coupling reaction is effected by a conventional reagent, for example N,N-dicyclohexylcarbodiimide, if appropriate in the presence of a tertiary base such as dimethylaminopyridine.

In general, the reactants are used in stoichiometric ratios except for the tertiary amine, which is used in an amount equal to about 1/10 of the alcohol because it is easier to remove the excess amino acid remaining in the ester, by washing with water, than to remove an excess of cycloalkanol. The reactions are performed in solvents which are inert towards the reactants, for example aliphatic halogenated hydrocarbons such as chloroform, methylene chloride or tetrachloroethane, or dimethylformamide, which has better solvent properties.

The reaction is started at a temperature around 0° C. and then continued under laboratory temperature conditions for several hours until the progress of the reaction, which is followed by thin layer chromatography, is sufficient. In general, an overnight reaction suffices to give a substantial yield. The ester formed is then isolated by the usual extraction and chromatography methods and the group protecting the α-nitrogen is removed. The conditions used for deprotection obviously depend on the blocking group present, it being possible for the medium to be anhydrous or aqueous and, if appropriate, alkaline or acid.

Of the protecting groups which are tested, the most recommended is the benzyloxycarbonyl radical, which can be removed under mild conditions by hydrogenolysis, this hydrogenolysis being performed in a secondary alcohol, for example isopropanol, or in acetic acid, in order to avoid transesterification.

The protecting group can also be a t-butoxycarbonyl radical, which can be removed by reaction with trifluoroacetic acid at low temperature so as not to degrade the primary alkyl ester.

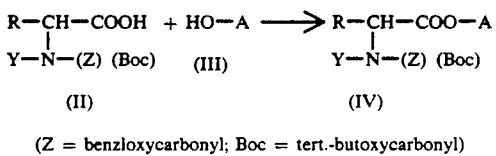

(Z = benzloxycarbonyl; Boc = tert.-butoxycarbonyl)

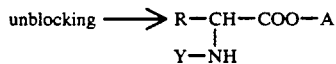

In the case where the amino acid contains a second reactive acid group, for example in the case of glutamic, aspartic and α-aminoadipic acids, it is essential to block the amino group as above and also the ω-carboxyl group.

This group can be blocked by the methods known in peptide synthesis, preferably by a benzyl ester group, which will be removed, after condensation, during the hydrogenolysis of the N-benzyloxycarbonyl radical (see Methoden der Organischen Chemie (Methods of Organic Chemistry), Houben Weyl, Synthese von Peptiden (Synthesis of Peptides) 15/1 p. 645).

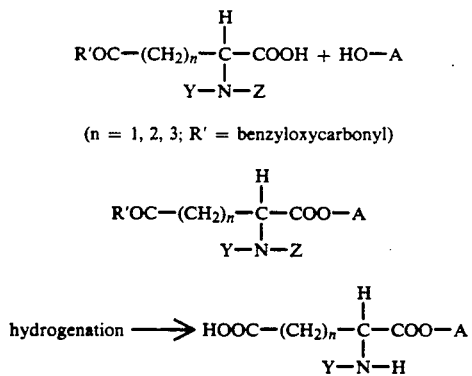

In the particular case where it is desired to obtain the α-cycloalkyl ester of aspartic, glutamic or aminoadipic acid while retaining a simple derivative of the ω-carboxyl group, namely a methyl or ethyl ester or a primary amide, the reaction merely has to be carried out with a derivative of the general formula (V) in which R′=OCH$_3$, OC$_2$H$_5$ or NH$_2$, following the same procedure; under these conditions, the alkyl ester or the amide in the ω-position of the dicarboxylic acid is not affected by hydrogenolysis.

In the case where the amino acid contains a second reactive —OH group (secondary alcohol or phenol), it is possible succesively to block the α-amino nitrogen with a benzyloxycarbonyl radical and the hydroxyl group with a benzyl ether or with a benzyloxycarbonyl ester in the case of a phenolic OH.

However, it has been found that, by working under particularly mild conditions (slow rate of introduction of reactants and low temperture), it is only essential to block the nitrogen carried by the carbon in the 2-position; this is particularly true for tyrosine and 5-hydroxytryptophan.

In the simpler case of polyamino acids, a poly-N-benzyloxycarbonyl derivative can be obtained simply by using sufficient amounts of benzyl chloroformate (see the reference cited above, p. 528, relating to arginine).

Hydrogenolysis, which can be performed in two steps if appropriate, leads to the derivative of the general formula (I).

In the case where Y represents an acetyl, propionyl or benzoyl radical in the general formula, it is no longer necessary to protect the nitrogen in the α-position and condensation of the N-acetylamino acid with the alcohol leads directly to the desired product:

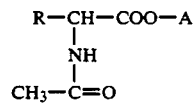

In the case where Y represents an acetyl, propionyl or benzoyl radical in the general formula and R contains a further reactive radical, namely —COOH, —NH$_2$ or —OH, the latter must be blocked prior to condensation and then unblocked by the methods described above.

In the case where Y determines a ring with R in the general formula (I), for example in the case of pyroglutamic acid:

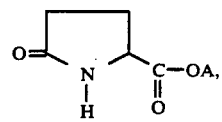

it is preferable, although not essential, to block the nitrogen of the pyrrolidine with a benzyloxycarbonyl radical prior to condensation of the pyroglutamic acid. The overall yield (blocking, condensation, unblocking) is actually higher than that obtained by direct condensation.

In the case where the amino acid is blocked by a radical of low lability, for example when Y=COCH$_3$ in the general formula (I) or in the case where R determines a pyrrolidin-2-one ring with Y, it is possible to carry out the esterification in the usual way in a solvent of the hydrocarbon type, for example toluene or xylene, at the reflux temperature, in the presence of an acid catalyst such as sulfuric acid or paratoluenesulfonic acid.

It is known that cholesterol is a substance vital to mammals, two-thirds of it being synthesized by the liver and one-third being provided by food.

Only a few percent of this lipophilic cholesterol is carried by the blood, encapsulated by lipoproteins such as the chylomicrons, VLDL, IDL, LDL and HDL.

A disorder of the blood cholesterol level, which is one of the causes of atherosclerosis, cannot always be corrected simply by changing the diet.

It is therefore essential to correct and regulate the production of cholesterol in the liver.

Now, 3-hydroxy-3-methylglutaric CoA reductase (HMG CoA reductase or HMGR), which ensures reduction to mevalonic acid, is the main factor regulating cholesterol production.

In fact, it is considered that the reduction HMG→mevalonic acid is the key step in the rate of cholesterol production.

Inhibition of this enzyme may therefore be a decisive means of reducing the serum cholesterol level.

John S. BARAN et al. (J. Med. Chem. 1985, 28, 597) noted the activity of 3-n-alkyl-3-hydroxyglutaric acids on the inhibition of HMGR.

This HMG CoA reductase activity can be measured "in vitro" on cultures of human fibroblasts by the method of BROWN and GOLDSTEIN (J. Biol. Chemist. 1974, 249, 789) or alternatively "in vivo" on rats by the technique of R. LANGDON (J. Lipid. Res. 1977, 18, 24).

20, 25-Diazacholesterol inhibits cholesterol synthesis (R. E. RANNEY, Proc. Soc. Exp. Biol. Med. 1964, 116, 999) and causes an increase in HMG CoA reductase which can be as much as 3 to 400% of the value in the control animals.

It is thus possible to check the activity of an inhibitor (R. J. CHORVAT, J. Med. Chem. 1985, 28, 195).

It is also possible to determine a Minimum Effective Dose (MED) required to lower the HMGR levels in pretreated rats by, for example, 25%.

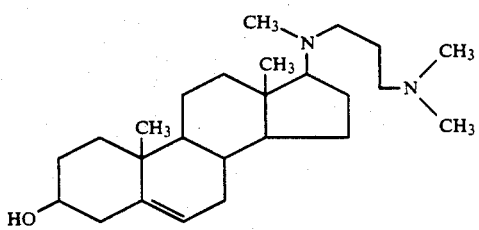

However, rats are poor models for studying molecules capable of inhibiting cholesterol synthesis by HMGR inhibition.

Furthermore, the lowering of the LDL level has been accepted as the therapeutic index for hypocholesterolemics.

An increase in the HDL's has sometimes been associated with mortalities due to cardiovascular incidents.

Certain drugs are capable of modifying cholesterol synthesis without producing a substantial variation in the serum levels of LDL and HDL.

The Applicant Company has discovered that the derivatives according to the present invention are particularly useful therapeutic agents in the correction of HMG dyslipemia, acting especially on the activity of HMG CoA reductase, the main factor of cholesterol synthesis.

The derivatives according to the present Application can be administered by themselves or in a mixture, as such or as pharmaceutically acceptable salts, in the various forms of administration known for drugs. Thus, such compounds can be administered enterally, parenterally or percutaneously, by themselves or in association with adjuvants or solvents used in the pharmaceutical industry, such as water, polyalkylene glycols, natural oils, starch and gelatin.

The solid pharmaceutical forms can be, for example, tablets, gelatin capsules, ordinary capsules or suppositories. The liquid forms can be solutions, suspensions or emulsions. The unit dose of the pharmaceutical preparation is between 10 and 1000 mg.

The non-limiting examples which follow describe the novel compounds in greater detail, together with the processes according to the present invention for their preparation and the results of the biochemical or pharmacological tests to determine their medicinal activities.

EXAMPLE I

Trimethylcyclohexyl L-Pyroglutamate (predominantly trans)

(a) 3,3,5-Trimethylcyclohexyl N-benzyloxycarbonyl-L-pyroglutamate 34.2 g (0.13 mol) of N-benzyloxycarbonyl-L-pyroglutamic acid (prepared according to Berichte 97, 2434 [1964] or Annalen 649, 183 [1961] ) are added to 150 ml of dimethylformamide, followed by 2 g of dimethylaminopyridine and then 18.48 g (0.13 mol) of 3,3,5-trimethylcyclohexanol (mixture of 90% trans isomer and 10% cis isomer) diluted in 50 ml of dimethylformamide. 26.8 g (0.13 mol) of dicyclohexylcarbodiimide are then run in over a period of about 15 minutes, the reaction medium being kept at $+5°$ C. The mixture is then stirred at room temperature for 24 hours, after which the solvent is evaporated off, the residue is taken up with dilute hydrochloric acid and extraction is carried out with chloroform.

After the organic layer has been washed until the washings are acid, basic and neutral, it is evaporated to dryness and the residue is purified by chromatography on a silica column with a chloroform/acetone mixture. The title derivative is obtained pure, in the form of a thick oil, with a yield of 65 to 70%.

(b) 3,3,5-Trimethylcyclohexyl L-pyroglutamate

The product obtained in the previous section is dissolved in 500 ml of isopropanol and hydrogenated in the presence of 5% palladium-on-charcoal at ordinary temperature and pressure. After filtration and evaporation of the solvent, the product is distilled under reduced pressure. Boiling point: 130° C./0.1 mm Hg.

The product shows a single spot in chromatography on a thin layer of silica (developing—vanillin, $H_2SO_4$). System toluene 10/ethyl formate 10/formic acid 1: Rf=0.45

System chloroform 25/acetone 7: Rf=0.50

$[\alpha]_D^{25} = -6.4°$ (C=1%, DMF)

NMR (in $CDCl_3$ relative to TMS): 4.2 ppm (m), 1H in the α-position to the C=O 2.3 ppm (m), 4H, —CH$_2$—CH$_2$—(pyrrolidine ring) 3.7 ppm (m), 1H, COO—CH between 1 and 2 ppm (m), 7H, cyclohexyl 1 ppm (s), 6H, (d), 3H, —CH$_3$.

EXAMPLE II

Direct Acylation of 3,3,5-Trimethylcyclohexanol with L-Pyroglutamic Acid 51.6 g (0.4 mol) of L-pyroglutamic acid and 50 g (0.35 mol) of trimethylcyclohexanol (enriched in trans isomer) are dissolved in 450 ml of dimethylformamide containing 2 g (16 millimol) of 4-dimethylaminopyridine, and 82.6 g (0.4 mol) of dicyclohexylcarbodiimide in 140 ml of dimethylformamide are then run in. The mixture is stirred for 24 h and evaporated, the residue is taken up with dilute hydrochloric acid, extraction is carried out with chloroform and the extract is washed with sodium carbonate and with water, dried and distilled (boiling point 140°-50°/0.2 mm Hg) to give a yield of 50%.

$[\alpha]_D^{25} = -6.4°$ (C=1%, DMF)

EXAMPLE III

Direct Esterification of 3,3,5-Trimethylcyclohexanol with Pyroglutamic Acid 26 g (0.2 mol) of pyroglutamic acid and 28 g (0.2 mol) of 3,3,5-trimethylcyclohexanol (enriched to 90% of trans isomer) are dissolved in 200 ml of dimethylformamide and 500 ml of toluene containing 2 ml of sulfuric acid. The solution is refluxed for 20 hours, with vigorous stirring, the water formed being progressively removed. After the solvent has been evaporated off, the residue taken up with chloroform and the mixture washed several times with water, the solvent is evaporated off in vacuo, followed by the unreacted trimethylcyclohexanol, and the title derivative is distilled at 160°-170°/0.7 mm Hg. The yield is 20% on average.

EXAMPLE IV 3,3,5-Trimethylcyclohexyl Pyroglutamate (predominantly cis)

The conditions of Example II are followed using 3,3,5-trimethylcyclohexanol enriched to 90% of its cis isomer.

The product is chromatographed on silica gel with a mixture of chloroform and ethanol.

After evaporation of the solvent, 25% of the title derivative is obtained in the form of a thick oil.

In TLC, the product shows a single spot in both the solvent systems described in Example I; the Rf is identical to that of the trans isomer (enriched).

$[\alpha]_D^{25} = -1.5°$ (C=1%, DMF)

Characteristic infrared bands: 3300–3200 cm$^{-1}$, unresolved signals; 2980–2820 cm$^{-1}$, CH$_2$-CH$_3$; 1730–1700 cm$^{-1}$ (vs).

EXAMPLE V

HYDROCHLORIDE OF THE L-GLUTAMINE ESTER OF 3,3,5-TRIMETHYLCYCLOHEXANOL (a) N-Benzyloxycarbonyl-L-glutamine ester of 3,3,5-trimethylcyclohexanol 16.10 g (57.5 millimol) of α-N-benzyloxycarbonyl-L-glutamine (prepared according to the general technique described in Methoden der Organischen Chemie (Methods of Organic Chemistry)—Houben Weyl—Synthese von Peptiden (Synthesis of Peptides) 15, 1, p. 701— Georg Thieme Verlag) are added to 100 ml of dimethylformamide, and 7.11 g (50 millimol) of 3,3,5-trimethylcyclohexanol (mixture of 90% trans isomer and 10% cis isomer) and 0.92 g (7.5 millimol) of 4-dimethylaminopyridine are then introduced. The mixture is cooled to between 0° and +5° and 11.9 g (57.5 millimol) of dicyclohexylcarbodiimide are introduced slowly.

The mixture is then stirred for 24 hours at ordinary temperature and evaporated to dryness. The residue is taken up with dilute hydrochloric acid and with chloroform, the treatment being the same as in Example I. The product is purified by chromatography on a silica column with a chloroform/isopropanol mixture.

This gives 70% of the title derivative in the pure state; in TLC on silica in the solvent system chloroform 30/isopropanol 2, it has an Rf of 0.30.

If the TLC is performed in the system toluene 10/ethyl formate 10/formic acid 1, it is possible to see the spots of both the trans and cis isomeric esters at Rf=0.52 and Rf=0.47 respectively.

By chromatography on a silica column with a chloroform/isopropanol mixture, it is possible to separate out the major part of the trans ester of Rf=0.52.

(b) 3,3,5-Trimethylcyclohexyl L-γ-amidoglutamate (trans)

The product obtained above is subjected to hydrogenolysis in isopropanol in the presence of palladium-on-charcoal. When the reaction is complete, the mixture is filtered and the filtrate is evaporated to give the title derivative in the form of a thick oil; in TLC in the system n-butanol 8/acetic acid 1/water 1, it shows a single spot of Rf=0.37.

By reaction with a solution of hydrogen chloride in ether, trans-3,3,5-trimethylcyclohexyl L-γ-amidoglutamate hydrochloride of m.p.=125°-129° C. can be obtained as crystals.

EXAMPLE VI

TRANS-3,3,5-TRIMETHYLCYCLOHEXYL L-α-GLUTAMATE HYDROCHLORIDE (a) 3,3,5-Trimethylcyclohexyl N-benzyloxycarbonyl-γ-benzyl-α-L-glutamate 37.1 g (0.1 mol) of N-benzyloxycarbonyl-γ-benzyl-L-glutamic acid prepared by the method of KLIEGER and GIBIAN (Annalen 655, 195, 1962) are added to 150 ml of dimethylformamide containing 1.5 g of 4-dimethylaminopyridine, and 14.2 g (0.1 mol) of 3,3,5-trimethylcyclohexanol are then introduced.

The mixture is cooled to between 0° and +5° C., with stirring, and 20.6 g (0.1 mol) of dicyclohexylcarbodiimide diluted in 200 ml of DMF are introduced, the temperature being kept below +5° C. The mixture is then stirred at ordinary temperature until the reaction is complete, as detected by TLC.

The solvent is evaporated off and the residue is then treated as in the previous experiments. After chromatography on a silica column, the title derivative is obtained in the pure state with a yield of 55%; in TLC on silica in the solvent system chloroform 30/isopropanol 2, it shows a single spot of Rf=0.35. In TLC in the system toluene 10/ethyl formate 10/formic acid 1, on the other hand, it is possible to see the ester of the trans form of 3,3,5-trimethylcyclohexanol at Rf=0.55 and the ester of the cis form at Rf=0.45. The ester is therefore chromatographed on a silica column in order to separate out the N-Z-γ-(OBz)-glutamic acid ester of trans-trimethylcyclohexanol, which shows a single spot at 0.55.

(b) 3,3,5-Trimethylcyclohexyl α-L-glutamate hydrochloride (trans)

The product obtained in the previous section is subjected to hydrogenolysis in isopropanol under ordinary temperature and pressure conditions in the presence of palladium-on-charcoal. This gives the title derivative in the pure state in the form of an amorphous oil; in TLC on silica, it shows a single spot of Rf=0.37 in the system n-butanol 10/acetic acid 1/water 1. This product can be converted to its hydrochloride by means of a solution of hydrogen chloride in ether, giving a well-crystallized product of m.p. 95°–100° C.

EXAMPLE VII

Magnesium Salt of 3,3,5-Trimethylcyclohexyl N-Acetyl-L-α-Aspartate (a) 3,3,5-Trimethylcyclohexyl N-acetyl-β-benzyl-L-α-aspartate 26.5 g (0.1 mol) of N-acetyl-β-benzyl-L-aspartic acid (prepared according to J. of Pharmaceutical Sciences 52, 9, 1963) are added to 150 ml of dimethylformamide containing 1.5 g of 4-dimethylaminopyridine, and 14.2 g (0.1 mol) of 3,3,5-trimethylcyclohexanol are then introduced. The mixture is cooled to between 0° and +5° C. and 20.6 g (0.1 mol) of dicyclohexylcarbodiimide diluted in 200 ml of DMF are run in. The subsequent treatment is the same as in Example VI-a. The title derivative is obtained as a mixture of both the cis and trans isomers, showing a single spot of Rf=0.25 in the system chloroform 30/isopropanol 2.

(b) Magnesium salt of 3,3,5-trimethylcyclohexyl N-acetyl-L-α-aspartate

The product obtained in the previous section is subjected to hydrogenolysis under the conditions of Example VI-b. After treatment, 3,3,5-trimethylcyclohexyl N-acetyl-L-aspartate is obtained in the form of a thick oil. The product is suspended in water and treated with magnesia until a pH of 6.0–7.0 is obtained. After filtration, the filtrate is evaporated in vacuo at low temperature to give the title derivative in the form of the magnesium salt.

The following derivatives are obtained by treating L-pyroglutamic acid with stoichiometric amounts of various substituted or unsubstituted cycloaliphatic alcohols, such as cyclohexanol, 3,5-dimethylcyclohexanol (cis/trans mixture), 3,5,5-trimethylcyclohex-2-en-1-ol, 1-methylcyclopentanol, terpin-4-enol and terpineol, under the conditions described in Example III:

| L-Pyroglutamate of | Boiling point |
|---|---|
| Example VIII cyclohexanol | 175° C./18 mm Hg |
| Example IX 3,5-dimethylcyclohexanol | 190–200° C./18 mm Hg |
| Example X 2,6-dimethylcyclohexanol | 190–200° C./18 mm Hg |
| Example XI 3,5,5-trimethylcyclohex-2-en-1-ol | 140° C./0.2 mm Hg |
| Example XII 1-methylcyclopentanol | 140° C./18 mm Hg |
| Example XIII terpin-4-enol | 120° C./0.1 mm Hg |
| Example XIV terpineol | 115–120° C./0.1 mm Hg |

EXAMPLE XV

Activity On The Experimental Hyperlipemia Induced By Triton

Groups of 10 fasted rats weighing about 200 g are treated with an intraperitoneal injection of Triton at a dose of 300 mg/kg; immediately afterwards, the products are administered orally.

After 18 hours, the cholesterol and triglycerides are determined. The results are shown in the following table:

| Treatment | Dose (mg/kg) | Triglyceride level (g/l) | | | Cholesterol level (g/l) | | |
|---|---|---|---|---|---|---|---|
| Control without Triton | | 0.62 | ± | 0.12 | 2.16 | ± | 0.30 |
| Control with Triton | — | 6.41 | | 2.60 | 5.04 | | 1.04 |
| Ref. nicotinic acid | 500 | 1.41 | | 0.31 | 5.00 | | 1.20 |
| Product of Ex. I | 150 | 0.93 | | 0.38 | 1.95 | | 0.36 |
| Product of Ex. I | 50 | 1.46 | | 0.47 | 2.80 | | 0.60 |
| Product of Ex. III | 150 | 1.10 | | 0.30 | 2.00 | | 0.33 |
| Product of Ex. IV | 150 | 0.85 | | 0.43 | 2.15 | | 0.61 |
| Product of Ex. V | 150 | 1.15 | | 0.27 | 1.95 | | 0.20 |
| Product of Ex. VI | 150 | 2.00 | | 0.30 | 2.50 | | 0.30 |
| Product of Ex. VII | 150 | 2.70 | | 0.40 | 3.00 | | 0.55 |
| Product of Ex. IX | 150 | 1.30 | | 0.33 | 2.10 | | 0.20 |
| Product of Ex. XI | 150 | 1.92 | | 0.41 | 2.00 | | 0.33 |
| Product of Ex. XIII | 150 | 2.10 | | 0.34 | 1.90 | | 0.52 |
| Product of Ex. XIV | 150 | 1.10 | | 0.19 | 2.12 | | 0.31 |

EXAMPLE XVI

Hypolipemic Activity In Rats Rendered Hyperlipemic With Olive Oil

A group of rats is placed on an atherogenic hyperlipemic diet enriched with olive oil and the animals are then treated per os. The cholesterol and triglycerides are then determined as in the previous example.

Cholesterol and triglycerides were obviously determined on animals which had originated from the same selection but had not been pretreated with Triton (control), and on animals which had been pretreated with Triton (hyperlip. control).

| Treatment | Dose (mg/kg) | Triglyceride level (g/l) | | | Cholesterol level (g/l) | | |
|---|---|---|---|---|---|---|---|
| Control | | 0.61 | ± | 0.10 | 2.38 | ± | 0.19 |
| Hyperlip. control | — | 2.45 | | 0.43 | 2.71 | | 0.92 |
| Product of Ex. I | 100 | 0.80 | | 0.29 | 1.50 | | 0.47 |
| Product of Ex. I | 25 | 1.39 | | 0.19 | 1.73 | | 0.24 |
| Product of Ex. III | 100 | 1.01 | | 0.37 | 1.47 | | 0.21 |
| Product of Ex. IV | 100 | 0.80 | | 0.42 | 1.47 | | 0.37 |
| Product of Ex. V | 100 | 0.92 | | 0.18 | 1.62 | | 0.42 |

EXAMPLE XVII

Determination Of The Inhibitory Activity Of The Compounds Towards 3-Hydroxy-3-Methylglutaryl Coenzyme A Reductase The method used is the one described by Shefer et al. (J. Lipid Res. 1972, 13, 402); cf, also Stokker (J. Med. Chem. 1985, 28, 357).

The 50% inhibitory doses are shown in the following table:

| TREATMENT | IC$_{50}$ (μM) |
|---|---|
| Product of Example I | 0.10 |
| Product of Example IV | 0.15 |
| Product of Example V | 0.08 |
| Product of Example VI | 0.12 |
| Product of Example VII | 0.50 |
| Product of Example VIII | 0.55 |
| Product of Example IX | 0.40 |
| Product of Example X | 0.40 |
| Product of Example XI | 0.13 |
| Product of Example XII | 0.60 |
| Product of Example XIII | 0.21 |
| Product of Example XIV | 0.30 |

What is claimed is:
1. Compounds of the formula

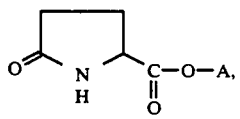

which is the pyroglutamic ester of 3, 3, 5-trimethylcyclohexanol.

2. A compound according to claim 1 wherein the A moiety is in an enriched form containing more than 90% of an isomer selected from the group consisting of the cis isomer and the trans isomer.

3. A compound according to claim 1 wherein the pyroglutamic acid is in the L configuration.

4. A method for combating lipemia disorders comprising administering to a mammal in need of said therapy a sufficient amount for combating lipemia disorders of a compound according to claim 1.

5. The method according to claim 4 wherein said lipemia disorder is hypercholesterolemia.

6. A method for regulating the production of cholesterol in the liver of a mammal comprising administering to said mammal an effective amount to regulate cholesterol production of a compound according to claim 1.

7. The method according to claim 6 wherein the cholesterol production is regulated by inhibiting HMG CoA reductase.

* * * * *